(12) United States Patent
Wee (10) Patent No.: US 11,793,954 B2
(45) Date of Patent: Oct. 24, 2023

(54) INHALATION DEVICE, SUBSTANCE STORAGE, INHALATION SYSTEM, AND METHOD OF OPERATING AN INHALATION DEVICE

(71) Applicant: Infineon Technologies AG, Neubiberg (DE)

(72) Inventor: Tue Fatt David Wee, Singapore (SG)

(73) Assignee: Infineon Technologies AG, Neubiberg (DE)

( * ) Notice: Subject to any disclaimer, the term of this patent is extended or adjusted under 35 U.S.C. 154(b) by 410 days.

(21) Appl. No.: 17/075,785

(22) Filed: Oct. 21, 2020

(65) Prior Publication Data

US 2021/0121647 A1    Apr. 29, 2021

(30) Foreign Application Priority Data

Oct. 24, 2019   (DE) .......................... 102019128730.8

(51) Int. Cl.
*A61M 15/00* (2006.01)

(52) U.S. Cl.
CPC ..... *A61M 15/0086* (2013.01); *A61M 2205/13* (2013.01); *A61M 2205/50* (2013.01); *A61M 2205/8206* (2013.01); *A61M 2205/8237* (2013.01)

(58) Field of Classification Search
None
See application file for complete search history.

(56) References Cited

U.S. PATENT DOCUMENTS

| | | | | |
|---|---|---|---|---|
| 2011/0265806 A1* | 11/2011 | Alarcon | .................. | A24F 47/00 131/273 |
| 2013/0306084 A1* | 11/2013 | Flick | ....................... | A24F 40/50 131/328 |
| 2014/0096781 A1* | 4/2014 | Sears | ...................... | A24F 40/50 131/328 |
| 2015/0101625 A1* | 4/2015 | Newton | .................. | A24F 40/60 131/329 |
| 2017/0013879 A1* | 1/2017 | Frisbee | ................ | A61M 11/042 |
| 2018/0153219 A1* | 6/2018 | Verleur | ................... | A24F 40/40 |
| 2019/0158938 A1* | 5/2019 | Bowen | .............. | H04M 1/72415 |
| 2019/0373679 A1* | 12/2019 | Fu | ........................ | H05B 3/0019 |

OTHER PUBLICATIONS

German Patent Office, Office Action issued for DE 102019128730.8, 13 pgs., dated Sep. 4, 2020.

* cited by examiner

*Primary Examiner* — Samchuan C Yao
*Assistant Examiner* — Tina Zhang
(74) *Attorney, Agent, or Firm* — Banner & Witcoff Ltd.

(57) ABSTRACT

An inhalation device including at least one processor configured to control an inhalation process including vaporing a substance received from a substance storage when coupled to the inhalation device, wherein the at least one processor is configured to be operated in an operation mode or in a standby mode, an electronic interface configured to be coupled to a substance storage interface, a passive detection circuit coupled between the electronic interface and the at least one processor and configured to detect whether the substance storage is coupled to the inhalation device, and, in case it is detected that the substance storage is coupled to the inhalation device, cause the at least one processor to switch from the standby mode to the operation mode.

15 Claims, 8 Drawing Sheets

INHALATION DEVICE, SUBSTANCE STORAGE, INHALATION SYSTEM, AND METHOD OF OPERATING AN INHALATION DEVICE

TECHNICAL FIELD

Various embodiments relate generally to an inhalation device, a substance storage, an inhalation system, and a method of operating an inhalation device.

BACKGROUND

Figure 1A:
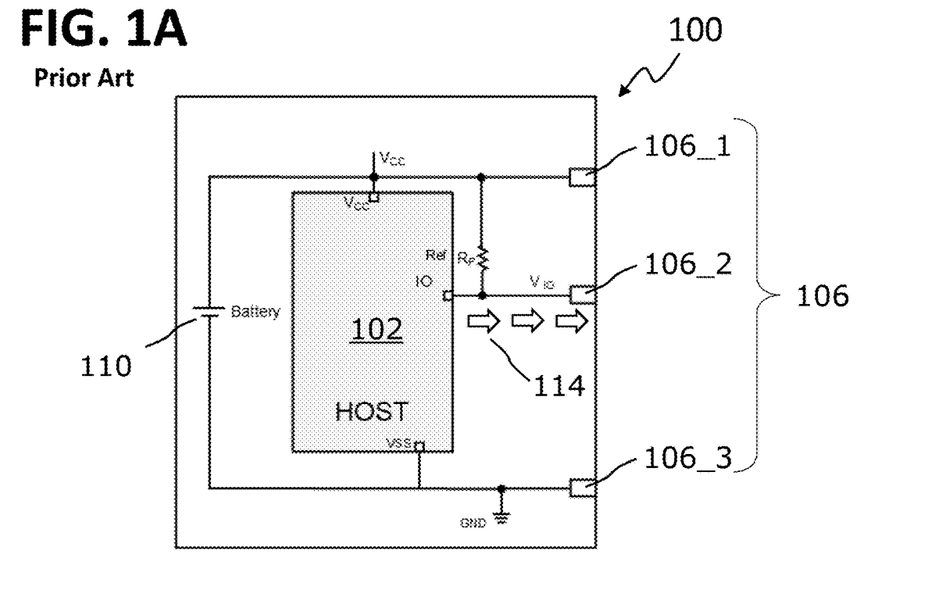
FIG. 1A and FIG. 1B show a conventional inhalation device and an inhalation system.
Figure 1B:
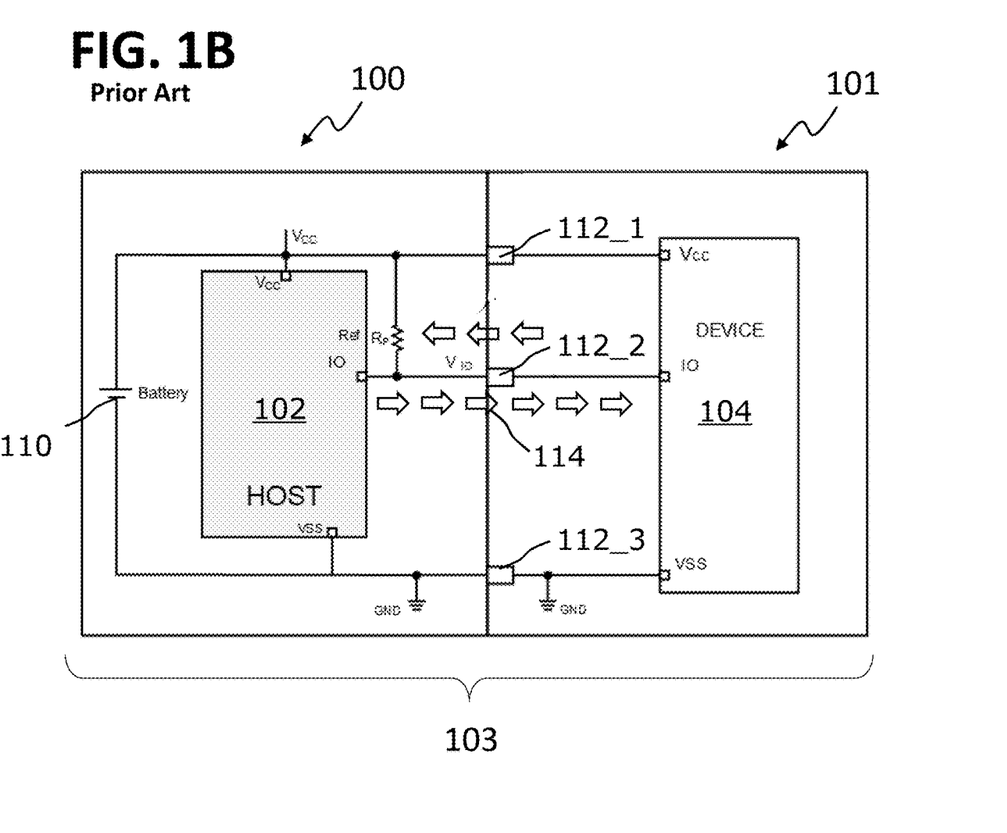

FIGS. 1A and 1B show a conventional inhalation device 100 and an inhalation system 103 including the inhalation device 100, also referred to as a host, and a substance storage 101, also referred to as a pod. Only when the substance storage 101 is connected to the inhalation device 100 may the inhalation device 100 be configured to receive a substance stored in the substance storage and vaporize it. For this, the inhalation device 100, e.g. an electronic circuit 102, may be configured to detect whether the substance storage 101 is connected to the inhalation device 100 (like in FIG. 1B) or not (like in FIG. 1A). The substance storage 101 of FIG. 1B may further include an electronic circuit 104 that may be configured to provide authentication information to the inhalation device 100, such that the substance may be provided to the inhalation device only upon successful authentication.

Therefore, at present, the inhalation device 100 may send a periodic signal 114 to one of its input/output ports 106_2 to poll for activities. For example, the host 100 may try to read a register and wait for a device—in other words, a register of the substance storage 101—to respond. If there is a response, this means that the pod 101 is attached to the host 100. If there is no response, then the pod 101 is not attached to the host 100.

A disadvantage of this scheme is that the inhalation device 100 is unable to enter an energy saving standby mode. This means that a battery 110 of the inhalation device 100 is constantly drained, which means that a user will have to recharge the inhalation device 100 quite often.

On the other hand, if the inhalation device 100 enters a standby mode to conserve energy, or is switched off for that purpose, when the substance storage (pod) 101 is attached to the inhalation device 100, the inhalation device may not know that the pod 101 is attached and may therefore fail to start an authentication procedure on the pod 101.

SUMMARY

An inhalation device may include at least one processor configured to control an inhalation process including vaporing a substance received from a substance storage when coupled to the inhalation device, wherein the at least one processor is configured to be operated in an operation mode or in a standby mode, an electronic interface configured to be coupled to a substance storage interface, a passive detection circuit coupled between the electronic interface and the at least one processor and configured to detect whether the substance storage is coupled to the inhalation device; and, in case it is detected that the substance storage is coupled to the inhalation device, cause the at least one processor to switch from the standby mode to the operation mode.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosure. In the following description, various embodiments of the disclosure are described with reference to the following drawings, in which.

DESCRIPTION

The following detailed description refers to the accompanying drawings that show, by way of illustration, specific details and embodiments in which the disclosure may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

In various embodiments, an inhalation device, e.g. a host (also referred to as base) of an electronic cigarette (e-cigarette), may be provided that may passively detect during a standby mode whether a substance storage, e.g. a pod containing a substance to be vaporized, is attached to the inhalation device or not.

Similarly, a substance storage in accordance with various embodiments that may allow an inhalation device in standby mode to passively detect its presence and an inhalation system including a substance storage and an inhalation device that may passively detect a presence of the substance storage while in standby mode may be provided.

Thereby, a power consumption of the inhalation device and the inhalation system, respectively, may be reduced. The substance storage may allow to use the inhalation device with the low power consumption.

In various embodiments, a method of operating an inhalation device (and of an inhalation system including the inhalation device and a substance storage) is provided that has an attach/detach scheme to detect the attachment of the substance storage to reduce the overall system power when the substance storage is not attached.

The method may allow the inhalation device, or more precisely a processor of the inhalation device, which may for example be an energy-hungry microcontroller, to enter standby mode when the substance storage is not attached, and may provide a low power supervisory circuit that can detect the attachment of the substance storage and "wake up" the inhalation device (i.e., the processor). By doing so, the inhalation device may be able to enter standby mode to conserve power.

Figure 2A:
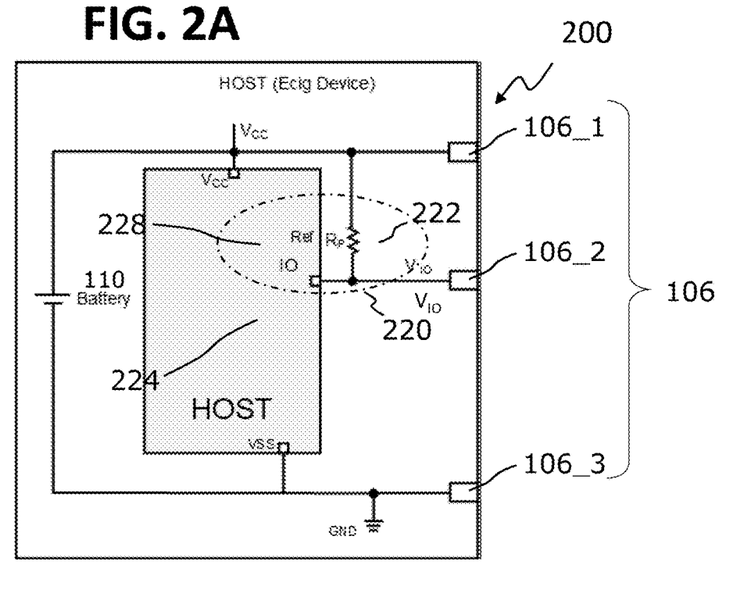
FIG. 2A and FIG. 2B show an inhalation device and an inhalation system in accordance with various embodiments, respectively.
Figure 2B:
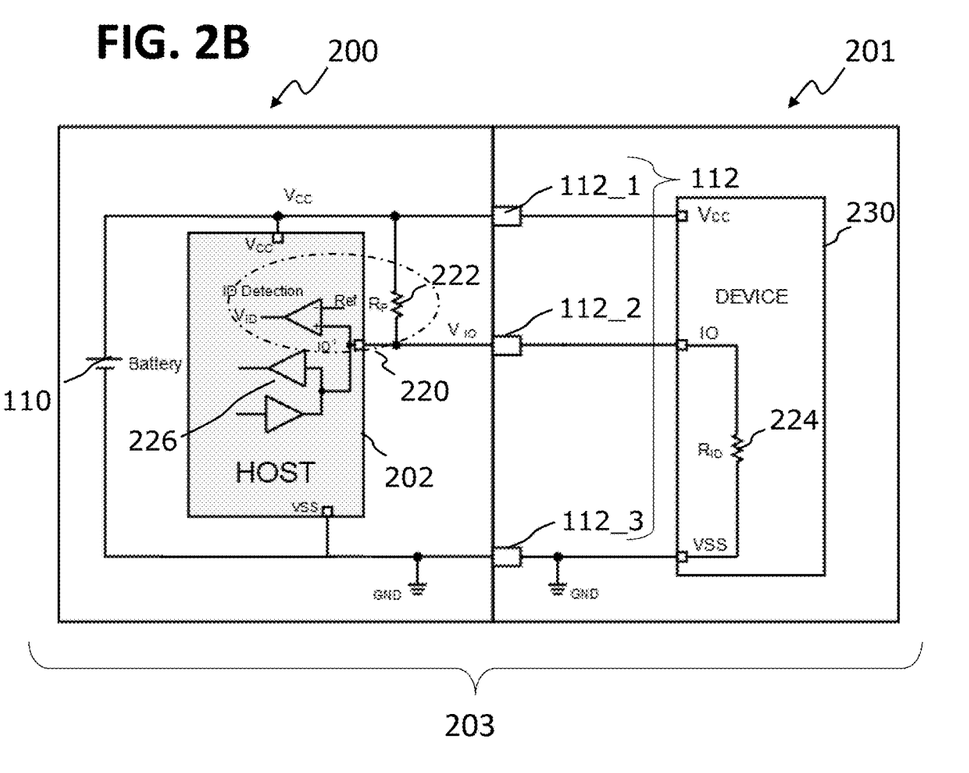
Figure 3:
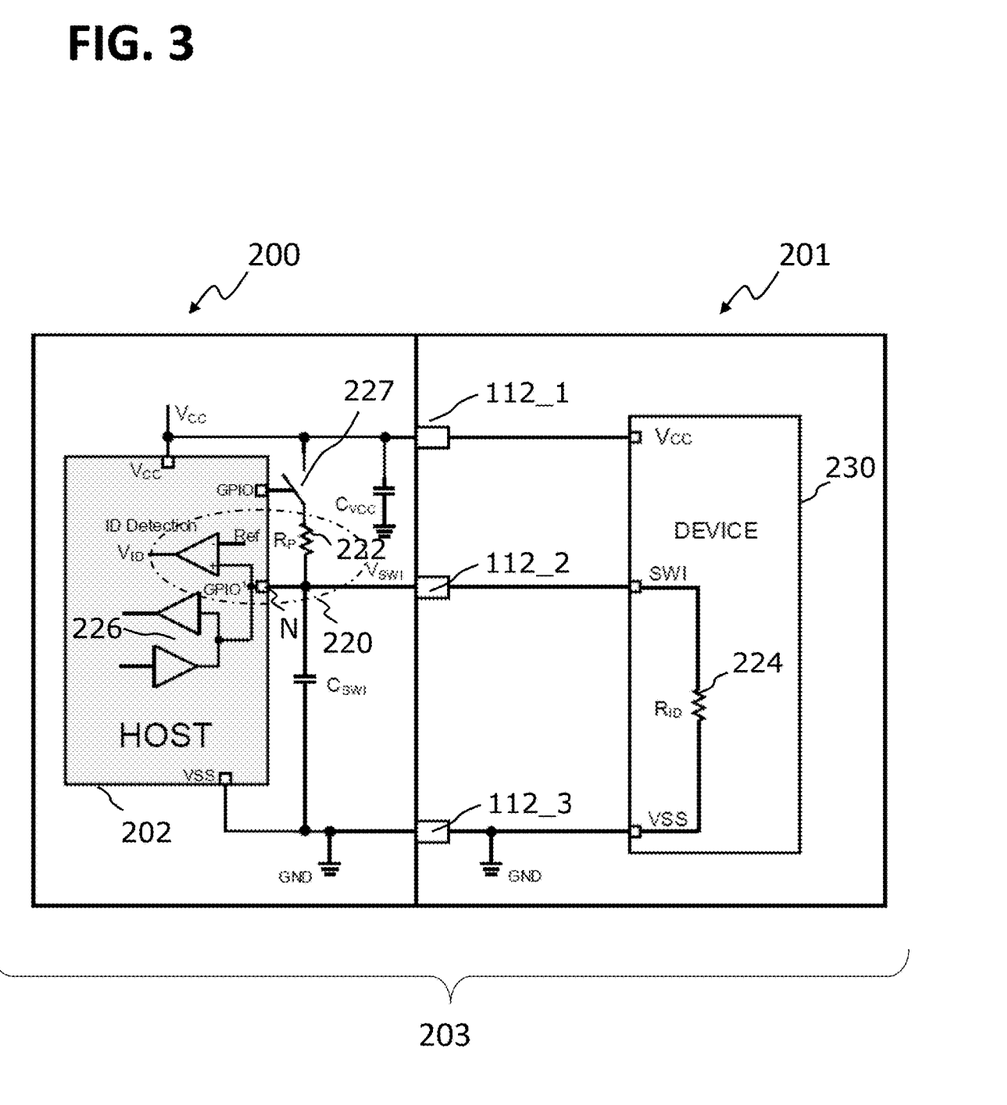
FIG. 3 shows an inhalation system in accordance with various embodiments.

FIG. 2A shows an inhalation device 200 in accordance with various embodiments. FIG. 2B shows an inhalation system 203 that includes the inhalation device 200 of FIG. 2A and a substance storage 201 in accordance with various embodiments, respectively. In other words, the inhalation device 200 with the substance storage 201 may form the inhalation system 203. FIG. 3 shows an inhalation system 203 in accordance with various embodiments.

The inhalation device 200 may include at least one processor configured to control an inhalation process including vaporing a substance received from a substance storage 201 when coupled to the inhalation device 200. To allow a better overview over the circuitry, some functional elements like the substance, the processor, a heater for vaporizing the substance, etc., have been omitted in the Figures. The processor may for example be part of an electronic circuit 202 that is indicated in FIG. 2A, FIG. 2B, and FIG. 3.

The at least one processor may be configured to be operated, e.g. alternatingly, in an operation mode and in a standby mode.

In various embodiments, the operation mode may mean that the inhalation device 200 is configured to vaporize the substance received from the substance storage 201. The operation mode may include intermittent vaporization. In other words, it may not include permanent vaporization. For example, a further start-of-vaporization signal may be required during operation mode to start vaporizing, e.g. a suction detection, a mouth/lip touch detection, or the like. In various embodiments, in operation mode, the inhalation device 200 may further be configured to authenticate the substance storage 201. The authentication may include receiving an authentication information from the substance storage 201 (wherein the authentication information may optionally be requested by the inhalation device 200, e.g. as described below), and comparing the authentication information, e.g. using the processor, to authentication reference data stored in the inhalation device 200. The inhalation device 200 may be configured to provide various other functionalities while in operation mode.

The standby mode may in various embodiments be a "deep sleep" mode. In other words, a power consumption of the inhalation device 200 may be low, e.g. negligible, zero, or essentially zero. While in standby mode, the inhalation device 200 may passively wait for an attachment of the substance storage 201. In other words, no signal is actively sent out by the inhalation device 200 to detect a presence of the substance storage 201.

Figure 5A:
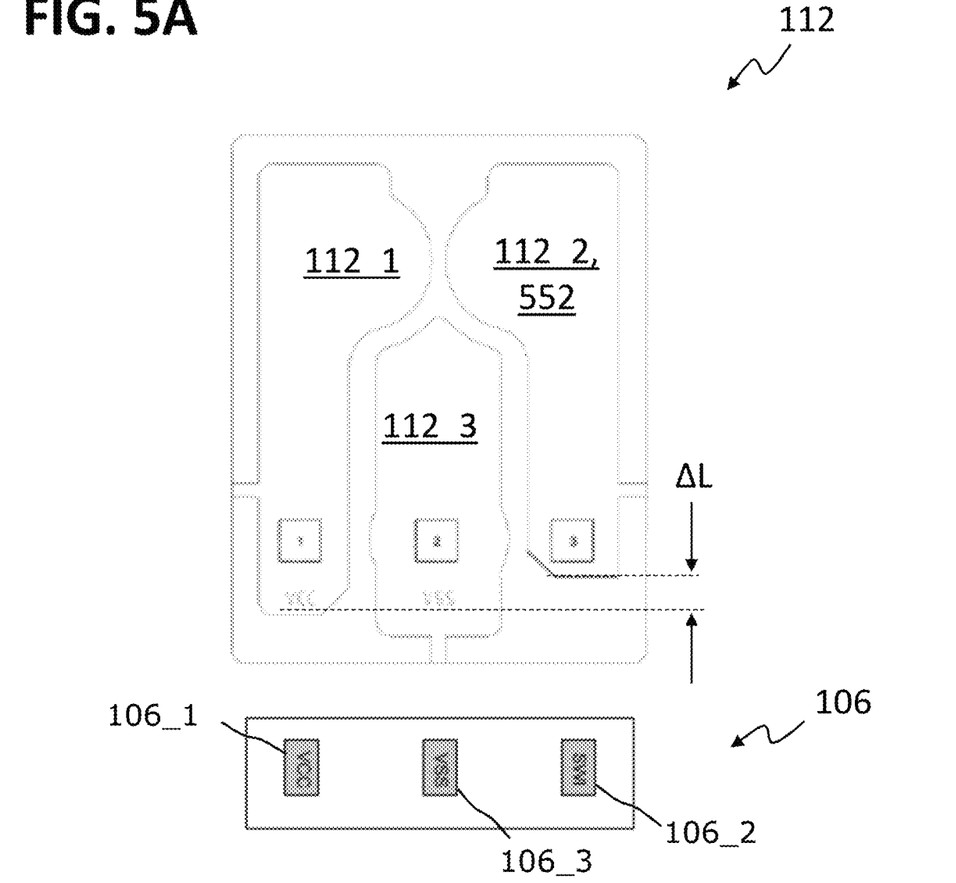
FIG. 5A shows a schematic configuration of contact surfaces of a substance storage and of an inhalation device, respectively, in accordance with various embodiments.

The inhalation device 200 may further include an electronic interface 106 that may be configured to be coupled to a substance storage interface 112. The electronic interface 106 may include a plurality of contact pads 106_1, 106_2, 106_3. The plurality of contact pads 106_1, 106_2, 106_3 may for example include (e.g., two) power contact pads 106_1, 106_3 (e.g., for providing a higher, e.g. positive voltage $V_{CC}$ and a lower voltage, e.g. ground, $V_{SS}$), and a signal contact pad 106_2. In the exemplary embodiments shown in FIGS. 2A, 2B and 3, the signal contact pad 106_2 is arranged between the power contact pads 106_1, 106_3, but any suitable arrangement may be provided, for example having the power contact pads 106_1, 106_3 side by side and the signal contact pad 106_2 next to one of them, e.g. as shown in FIG. 5A, where the contact pad for $V_{SS}$ is the middle contact pad. The plurality of contact pads 106_1, 106_2, 106_3 may be configured to provide power to the substance storage 201, e.g. through the power contact pads 106_1, 106_3 and corresponding power contact pads 112_1, 112_3 of the substance storage 201, and to exchange signals with the substance storage 201, e.g. through the signal contact pad 106_2 and a corresponding signal contact pad 112_2 of the substance storage 201. The power provided to the substance storage 201 may be used for driving an electronic circuit 230, e.g. an integrated circuit, e.g. a PCB, in the substance storage 201, for driving a valve to release the stored substance, and/or for other purposes.

The inhalation device 200 may further include a passive detection circuit 220 coupled between the electronic interface 106 and the at least one processor. The passive detection circuit 220 may be configured to detect whether the substance storage 201 is coupled to the inhalation device 200, and, in case it is detected that the substance storage 201 is coupled to the inhalation device 200, to cause the at least one processor to switch from the standby mode to the operation mode. In other words, it may be the (static) connection between the substance storage 201 and the inhalation device 200 and/or the process of connecting the substance storage 201 to the inhalation device 200 that may cause the detection of the substance storage 201 in the inhalation device 200 (e.g., in the passive detection circuit 220.

In various embodiments, the passive detection circuit 220 may include a pull-up or a pull-down resistor 222 to detect whether the substance storage 201 is coupled to the inhalation device 200. In FIG. 2B, an exemplary pull-up resistor 222 (which may be connected to a power source in the host board and may be pulled up to $V_{CC}$ level, wherein the power source may be powered by a (rechargeable) battery 110) is shown.

Figure 4:
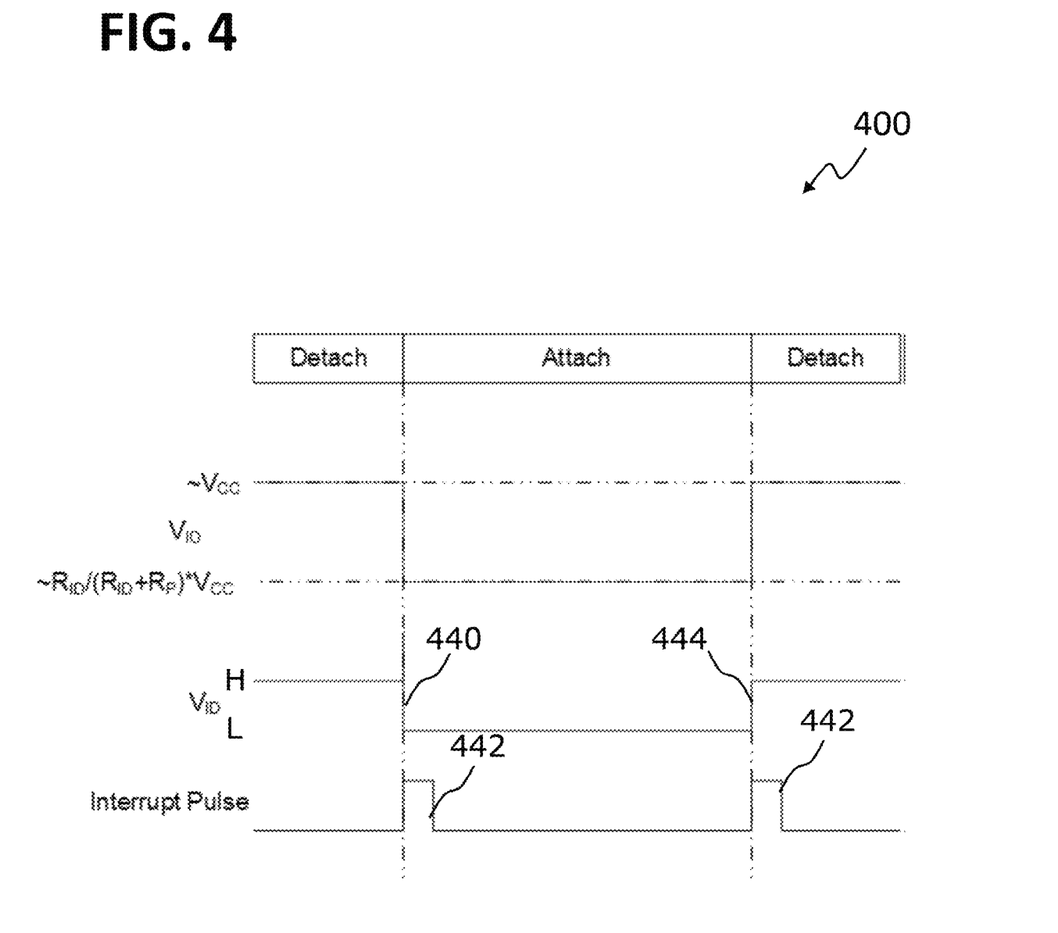
FIG. 4 shows signal levels at a circuit node of a circuit in the inhalation device during periods of its detachment from and attachment to, respectively, a substance storage in accordance with various embodiments.

FIG. 4 shows a signal diagram 400 with signal levels, e.g., voltages, at a circuit node N, e.g. at a general purpose input/output pin of the circuit 202 (e.g. an integrated circuit 202, e.g. a printed circuit board, PCB) in the inhalation device 200 (e.g. as in FIGS. 2A and 2B) during periods of its disconnection (detachment from) and connection (attachment) to the substance storage 201, respectively, in accordance with various embodiments, e.g. as in FIG. 2B. In the exemplary example of FIG. 2A and FIG. 2B, the voltage at the circuit node N may be at, nearly at, or around the higher voltage VCC of the two supply voltages VSS, VCC, because the pull-up resistor 222 is connected between the passive detection circuit 220 and VCC. Upon connection of the substance storage 201 to the inhalation device 200, the power contact pads 106_1, 106_3 of the inhalation device 201 may contact the corresponding power contact pads 112_1, 112_3 of the substance storage 201, and the signal contact pad 106_2 of the inhalation device 200 may contact the corresponding signal contact pad 112_2 of the substance storage 201.

In various embodiments, a further resistor 224 may be coupled between the $V_{SS}$ contact pad 112_3 and the signal contact pad 112_2 of the substance storage 201. Thereby, the further resistor 224 is connected to the circuit node N, and a voltage at the circuit node N may be altered, in this case lowered. As shown in FIG. 4, the altered voltage at the circuit node N (referred to as $V_{IO}$ in FIG. 4) during connection may be $R_{IO}/(R_{IO}+R_P) \times V_{CC}$, wherein $R_P$ is a resistance of the resistor 222, and $R_{IO}$ is a resistance of the further resistor 224. Upon removal of the substance storage 201, the voltage $V_{IO}$ at the circuit node N returns to its initial value at, nearly at or around $V_{CC}$. This means that the connection/disconnection of the substance storage 201 is passively detected by the passive detection circuit 220.

In various embodiments, the passive detection circuit 220 may further include a comparator 228, to which the voltage VIO may be provided to be compared to a reference voltage Ref. A voltage level of the reference voltage Ref may depend on the voltage VCC and a selection of the resistances of the resistors 222 and 224. The comparison in the comparator 228 may lead to a connected/disconnected signal VID having a predefined attachment voltage level L and a predefined detachment voltage level H, for example H=1V and L=0V. The rising/falling edges 444/440 of the connected/disconnected signal VID may be used to generate an interrupt signal, e.g. an interrupt pulse 442, for example as shown in FIG. 4. The interrupt pulse 402 may be used as a wake-up signal or a go-to-sleep signal for the processor to change from the standby mode to the operation mode or vice versa. In other words, if the substance storage 201 is attached to the inhalation device 200, the voltages VIO and VID, respectively, may drop from their respective high level to the respective low level, and the interrupt pulse 442 may be generated, which may switch the processor from the standby mode to the operation mode. If the substance storage 201 is detached from the inhalation device 200, the voltages VIO, and VID, respectively, may rise from their respective low level to the respective high level, and the interrupt pulse 442, which may be identical or essentially identical to the interrupt pulse 442 created during attachment, may be generated, which may switch the processor from the operation mode to the standby mode. In other words, identical or essentially identical interrupt pulses 442 may be used to switch the processor between its two states.

In various embodiments, the comparator 228 may be omitted and the rising/falling voltage signal $V_{IO}$ may be directly used as the trigger signal to form the interrupt pulse.

In various embodiments, instead of providing the resistor 222 as the pull-up resistor, the resistor 222 may be connected between the passive detection circuit 220 and $V_{SS}$ as a pull-down resistor. Consequently, the further resistor 224 may be coupled between the $V_{CC}$ contact pad 112_1 and the signal contact pad 112_2 of the substance storage 201. When the substance storage 201 is connected to the inhalation device 200, the further resistor 224 is connected to the circuit node N, and a voltage at the circuit node N may be altered, in this case raised. The rising/falling edges may, similar to what was described above for the pull-down resistor 222, be used as trigger signals for the forming of the interrupt signal to switch the processor from standby mode to operation mode and vice versa.

In various embodiments, the inhalation device 200 may further include a switch 227 coupled between the passive detection circuit 220 and a power supply of the inhalation device to couple or decouple the passive detection circuit 220 to or from the power supply 110. This is shown in FIG. 3 in an exemplary embodiment that is otherwise similar to the embodiment shown in FIG. 2B.

As mentioned above, after switching the processor to operation mode, the inhalation device 200 may be configured to authenticate the substance storage 201. For this, the authentication device may be configured to request and receive authentication information from the substance storage 201, and to authenticate the substance storage 201. The request for information may be sent and the returning information may be received by a transceiver 226 that may be part of the inhalation device 200, for example as shown in FIG. 2A, FIG. 2B, and FIG. 3.

Figure 5B:
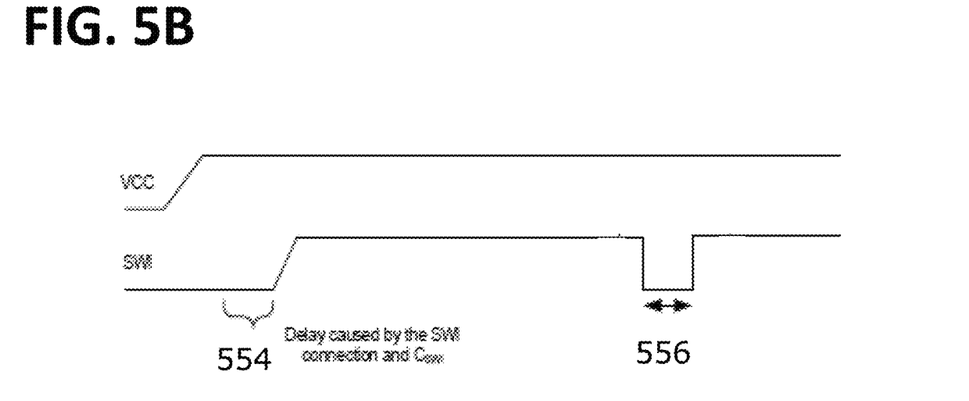
FIG. 5B shows signal levels generated in the substance storage during an attachment of the substance storage having the contact surfaces of FIG. 5A to the inhalation device in accordance with various embodiments.

FIG. 5A shows a schematic configuration of contact surfaces 112 of a substance storage 201 and contact pads 106 of an inhalation device 200, respectively, in accordance with various further embodiments. The substance storage 201 may include an electronic circuit, e.g. an integrated circuit similar to the electronic circuit 230 of FIG. 2B and FIG. 3, but without the resistor $R_{ID}$, and instead with an interrupt generation circuit. FIG. 5B shows signal levels generated in the substance storage 201, e.g. at its $V_{CC}$ pin and its SWI pin (or corresponding circuit nodes), respectively, during an attachment of the substance storage 201 having the contact surfaces of FIG. 5A to the inhalation device 200 in accordance with various embodiments.

As shown in FIG. 5A, the signal contact pad 112_2 (SWI) may be shorter than the power contact pad 112_1 ($V_{CC}$) by a length ΔL. This means that, upon connection of the substance storage 201 to the inhalation device 200, a voltage at the $V_{CC}$ pin rises first to the $V_{CC}$ voltage level, and a voltage at the SWI pin rises to an SWI voltage level with a delay 554 that may be caused by the shortened signal contact pad 112_2.

The electronic circuit 230 of the substance storage 201 may in various embodiments be configured to generate a pulse, e.g. an interrupt pulse 556 and to provide it at the signal contact pad 112_2. The passive detection circuit 220 of the inhalation device 200 may be configured to pass the pulse 556, which it may receive through its signal contact pad 106_2, to the processor to switch it from the standby mode to the operation mode, or the passive detection circuit 220 may convert the pulse 556 to an interrupt signal, using the falling and/or rising edge of the pulse as a trigger signal, and may provide the generated interrupt signal to the processor to switch it from the standby mode to the operation mode. Upon removal of the substance storage 201, the voltage level at the signal contact pad 106_2 may drop again abruptly, in other words, a response from the substance storage 201 may be missing, which may be detected by the passive detection circuit 220 and used as the trigger signal to generate another interrupt signal to switch the processor from operation mode to standby mode.

Figure 6:
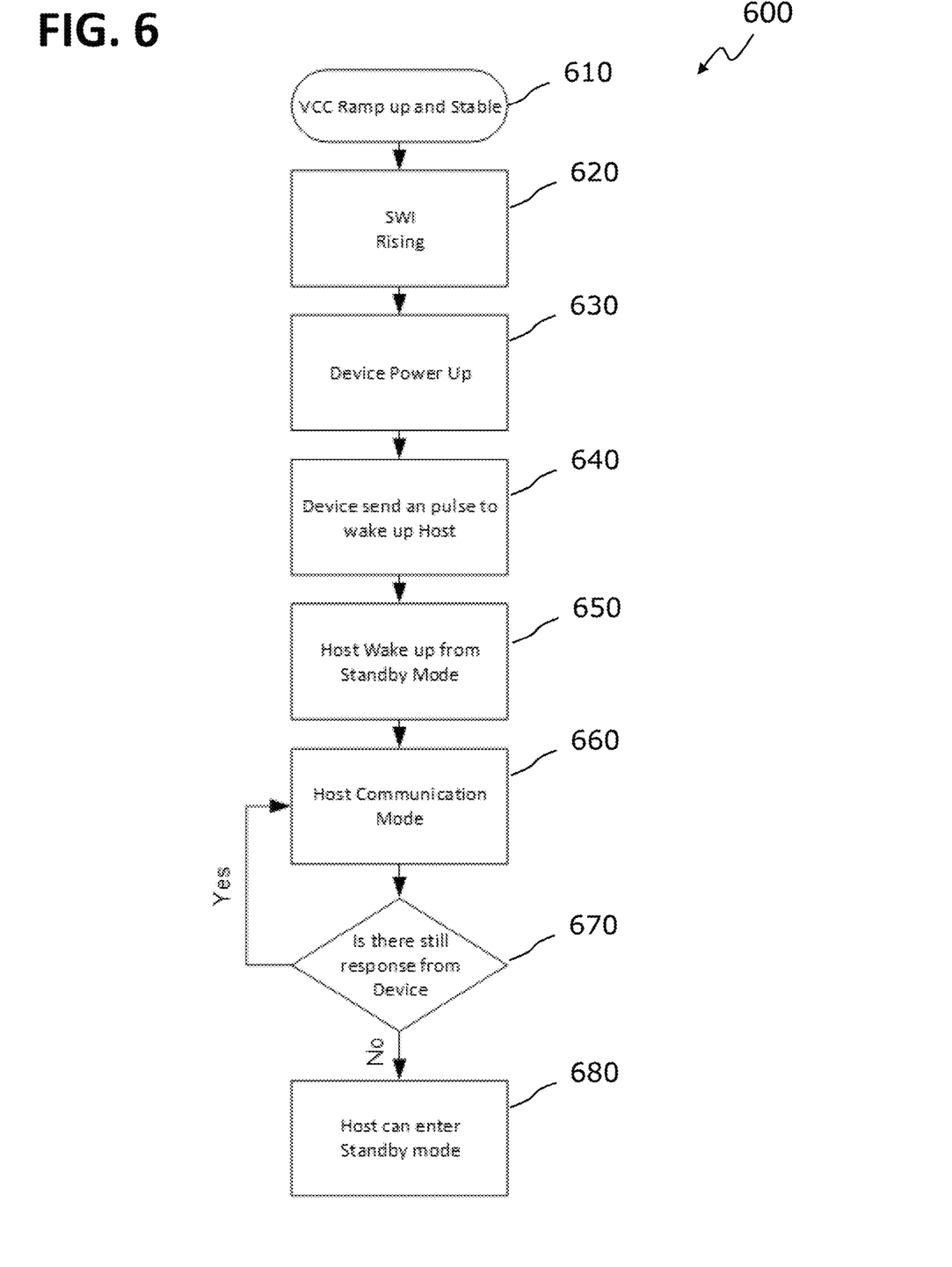
FIG. 6 shows a flow diagram of a method of operating an inhalation device in accordance with various embodiments having the contact surface configuration of FIG. 5A.

FIG. 6 shows a flow diagram 600 of a method of operating an inhalation system in accordance with various embodiments, for example as described in context with FIG. 5A and FIG. 5B.

The method may include (in the substance storage 201) ramping up the $V_{CC}$ signal and stabilizing it (in 610), raising the voltage level at the SWI pin (in 620), powering up the device, i.e. the electronic circuit of the substance storage (in 630), sending a pulse from the electronic circuit of the substance storage to the host, i.e. the inhalation device (in 640), waking up the host from standby mode to operation mode (in 650), taking up communication operations, in other words setting the host to a communication mode, which may be a sub-mode of the operation mode (in 660), and checking if there is still a response from the substance storage, and if yes, continue the communication mode, and if no, send the host back to standby mode (in 670).

Figure 7:
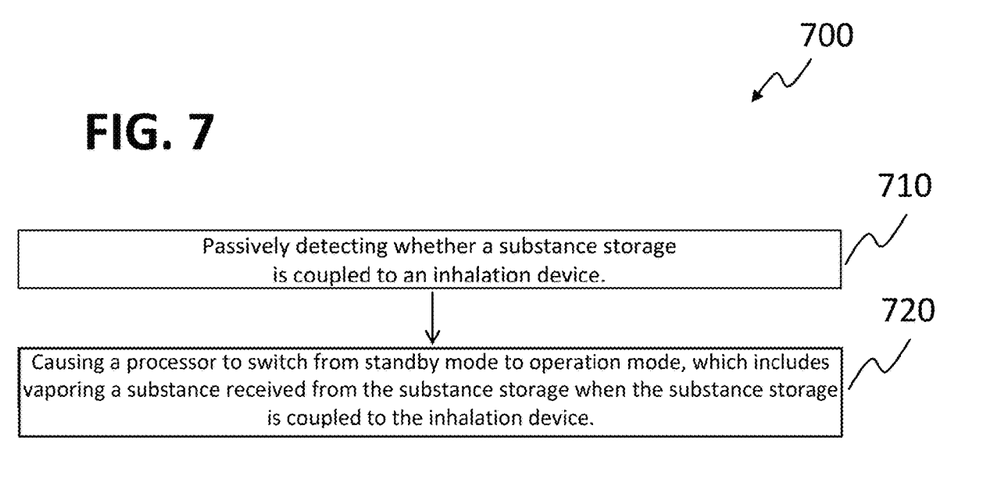
FIG. 7 shows a flow diagram of a method of operating an inhalation device in accordance with various embodiments.

FIG. 7 shows a flow diagram 700 of a method of operating an inhalation device in accordance with various embodiments.

The method may include passively detecting whether a substance storage is coupled to the inhalation device (in 710), and, in case it is detected that the substance storage is coupled to the inhalation device, cause the at least one processor to switch from a standby mode to an operation mode, wherein the operation mode includes vaporing a substance received from a substance storage when coupled to the inhalation device (in 720).

Figure 8:
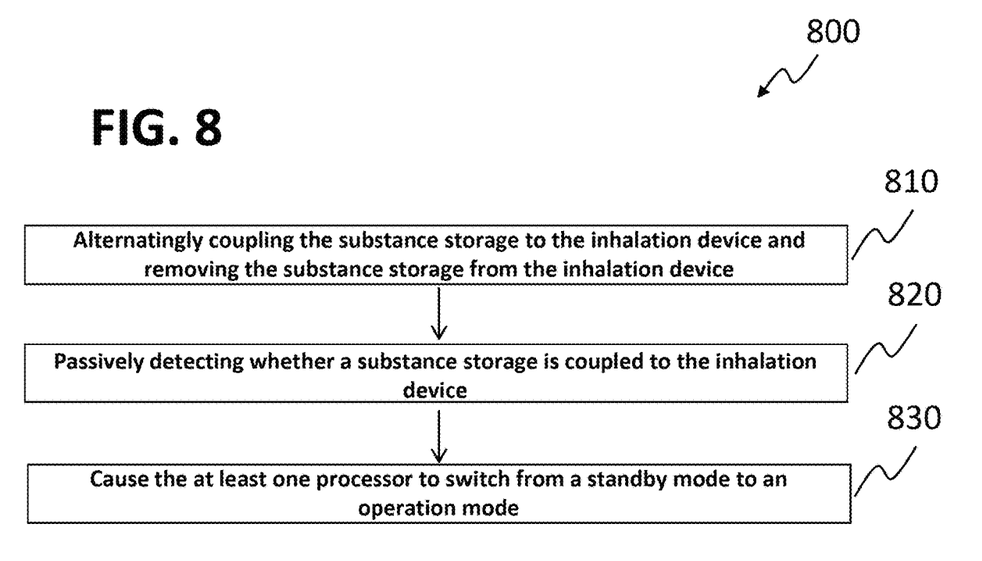
FIG. 8 shows a flow diagram of a method of operating an inhalation system in accordance with various embodiments.

FIG. 8 shows a flow diagram 800 of a method of operating an inhalation system in accordance with various embodiments.

The method may include alternatingly coupling the substance storage to the inhalation device and removing the substance storage from the inhalation device (in 810), passively detecting whether a substance storage is coupled to the inhalation device (in 820), and, in case it is detected that the substance storage is coupled to the inhalation device, cause the at least one processor to switch from a standby mode to an operation mode, wherein the operation mode includes vaporing a substance received from a substance storage when coupled to the inhalation device (in 830)

Various examples will be illustrated in the following:

Example 1 is an inhalation device. The inhalation device may include at least one processor configured to control an inhalation process including vaporing a substance received from a substance storage when coupled to the inhalation device, wherein the at least one processor is configured to be operated in an operation mode or in a standby mode, an electronic interface configured to be coupled to a substance storage interface, a passive detection circuit coupled between the electronic interface and the at least one processor and configured to detect whether the substance storage is coupled to the inhalation device; and, in case it is detected that the substance storage is coupled to the inhalation device, cause the at least one processor to switch from the standby mode to the operation mode.

In Example 2, the subject-matter of Example 1 may optionally further include that the passive detection circuit comprises a pull-up or a pull-down resistor to detect whether the substance storage is coupled to the inhalation device.

In Example 3, the subject-matter of Example 1 or 2 may optionally further include a switch coupled between the passive detection circuit and a power supply of the inhalation device to couple or decouple the passive detection circuit to or from the power supply.

In Example 4, the subject-matter of any of Examples 1 to 3 may optionally further include a power supply.

In Example 5, the subject-matter of Example 4 may optionally further include that the power supply includes a battery that is optionally rechargeable.

In Example 6, the subject-matter of any of Example 1 to 5 may optionally further include that the passive detection circuit is configured to provide a wake-up signal to the at least one processor.

In Example 7, the subject-matter of Example 6 may optionally further include that the wake-up signal is an interrupt pulse.

In Example 8, the subject-matter of any of Examples 1 to 7 may optionally further include that the passive detection circuit is configured to have, at a circuit node, a voltage having a first value in the case that the substance storage is decoupled from the inhalation device, and a second value different from the first value in the case that the substance storage is coupled to the inhalation device.

In Example 9, the subject-matter of any of Examples 1 to 8 may optionally further include an authentication device configured to request and receive authentication information from the substance storage after the switching from standby mode to operation mode, and to authenticate the substance storage.

In Example 10, a substance storage for coupling to an inhalation device is provided, including a substance storage container configured to contain a liquid inhalation substance, comprising a control device for controlling a release of the liquid inhalation substance, a substance storage interface configured to be coupled to an electronic interface of the inhalation device, and an passive detection circuit coupled between the substance storage interface and the substance storage container and configured cause the control device to release the liquid inhalation substance upon request from the inhalation device, wherein the passive detection circuit comprises a resistor coupled between two terminals of the substance storage interface and configured to cause the inhalation device to detect whether the substance storage is coupled to the inhalation device.

In Example 11, a substance storage for coupling to an inhalation device is provided, including a substance storage container configured to contain a liquid inhalation substance, a control device for controlling a release of the liquid inhalation substance, a substance storage interface with a plurality of first contact pads configured to be coupled to a plurality of second contact pads of an electronic interface of the inhalation device, and an electronic circuit coupled between the substance storage interface and the substance storage container and configured cause the control device to release the liquid inhalation substance upon request from the inhalation device, wherein the first contact pads include power contact pads and a signal contact pad, wherein the power contact pads are configured to contact power contact pads of the second contact pads before the signal contact pad contacts a signal contact pad of the second contact pads, and wherein the electronic circuit is configured to generate an interrupt signal in a case of time delay between a contacting of the power contact pads to the power contact pads of the second contact pads and a contacting of the signal contact pad to the signal contact pad of the second contact pads.

In Example 12, the subject matter of Example 11 may further include that the electronic circuit is further configured to generate an interrupt signal in a case of time delay between a loss of contact of the signal contact pad to the signal contact pad of the second contact pads and a loss of contact of the power contact pads to the power contact pads of the second contact pads.

Example 13 is an inhalation system. The inhalation system may include an inhalation device according to any of Examples 1 to 9, and a substance storage according to Example 10 wherein the substance storage is configured to be repeatedly couplable to and removable from the inhalation device.

Example 14 is a method of operating an inhalation device. The method may include passively detecting whether a substance storage is coupled to the inhalation device, and, in case it is detected that the substance storage is coupled to the inhalation device, cause the at least one processor to switch from a standby mode to an operation mode, wherein the operation mode includes vaporing a substance received from a substance storage when coupled to the inhalation device.

In Example 15, the subject-matter of Example 14 may optionally further include that the passively detecting includes pulling up or pulling down a voltage signal to detect whether the substance storage is coupled to the inhalation device.

In Example 16, the subject-matter of Example 14 or 15 may optionally further include coupling or decoupling the passive detection circuit to or from the power supply using a switch.

In Example 17, the subject matter of any of claims 14 to 16 may optionally further include providing a wake-up signal to at least one processor of the inhalation device.

In Example 18, the subject-matter of Example 17 may optionally further include that the wake-up signal is an interrupt pulse.

In Example 19, the subject-matter of any of Examples 14 to 18 may optionally further include providing a voltage having a first value in the case that the substance storage is decoupled from the inhalation device, and a second value different from the first value in the case that the substance storage is coupled to the inhalation device.

In Example 20, the subject-matter of any of Examples 14 to 18 may optionally further include requesting and receiving authentication information from the substance storage after the switching from standby mode to operation mode, and authenticating the substance storage.

Example 21 is a method of operating an inhalation system. The inhalation system may include a substance storage and an inhalation device, and the method may include alternatingly coupling the substance storage to the inhalation device and removing the substance storage from the inhalation device, passively detecting whether a substance storage is coupled to the inhalation device, and, in case it is detected that the substance storage is coupled to the inhalation device, cause the at least one processor to switch from a standby mode to an operation mode, wherein the operation mode comprises vaporing a substance received from a substance storage when coupled to the inhalation device.

While the disclosure has been particularly shown and described with reference to specific embodiments, it should be understood by those skilled in the art that various changes in form and detail may be made therein without departing from the spirit and scope of the disclosure as defined by the appended claims. The scope of the disclosure is thus indicated by the appended claims and all changes which come within the meaning and range of equivalency of the claims are therefore intended to be embraced.

What is claimed is:

1. An inhalation device, comprising:
   at least one processor configured to control an inhalation process comprising vaporing a substance received from a substance storage when coupled to the inhalation device, wherein the at least one processor is configured to be operated in an operation mode or in a standby mode;
   an electronic interface configured to be coupled to a substance storage interface;
   a passive detection circuit coupled between the electronic interface and the at least one processor, and configured to:
      detect whether the substance storage is coupled to the inhalation device; and
      in case the electronic interface detects that the substance storage is coupled to the inhalation device, cause the at least one processor to switch from the standby mode to the operation mode,
   wherein the passive detection circuit comprises a pull-up or a pull-down resistor to detect whether the substance storage is coupled to the inhalation device; and
   an authentication device configured to request and receive authentication information from the substance storage after the switching from the standby mode to the operation mode, and to authenticate the substance storage.

2. The inhalation device of claim 1, further comprising:
   a switch coupled between the passive detection circuit and a power supply of the inhalation device to couple or decouple the passive detection circuit to or from the power supply.

3. The inhalation device of claim 1, further comprising:
   a power supply.

4. The inhalation device of claim 3,
   wherein the power supply comprises a battery that is rechargeable.

5. The inhalation device of claim 1,
   wherein the passive detection circuit is configured to provide a wake-up signal to the at least one processor.

6. The inhalation device of claim 5,
   wherein the wake-up signal is an interrupt pulse.

7. The inhalation device of claim 1,
   wherein the passive detection circuit is configured to have, at a circuit node, a voltage having a first value in the case that the substance storage is decoupled from the inhalation device, and a second value different from the first value in the case that the substance storage is coupled to the inhalation device.

8. An inhalation system, comprising:
   an inhalation device comprising at least one processor, an electronic interface, and a passive detection circuit coupled between the electronic interface and the at least one processor;
   a substance storage couplable to the inhalation device, and comprising a substance storage container configured to contain a liquid inhalation substance, a substance storage interface configured to be coupled to the electronic interface of the inhalation device, and an electronic circuit coupled between the substance storage interface and the substance storage container,
   wherein the at least one processor is configured to control an inhalation process comprising vaporing the substance when received from the substance storage when coupled to the inhalation device, and to be operated in an operation mode or in a standby mode, and
   wherein the passive detection circuit comprises a pull-up resistor or a pull-down resistor coupled between two terminals of the substance storage interface and configured to cause the inhalation device to detect whether the substance storage is coupled to the inhalation device, and in case the passive detection circuit detects that the substance storage is coupled to the inhalation device, cause the at least one processor to switch from the standby mode to the operation mode; and
   an authentication device configured to request and receive authentication information from the substance storage after the switching from the standby mode to the operation mode, and to authenticate the substance storage,
   wherein the substance storage container comprises a control device configured to control a release of the liquid inhalation substance, and wherein the electronic circuit of the substance storage is configured to cause the control device to release the liquid inhalation substance upon request from the inhalation device.

9. A method of operating an inhalation device, comprising:
  passively detecting, by a passive detection circuit, whether a substance storage is coupled to the inhalation device, by pulling up or pulling down a voltage signal;
  in case the passive detection circuit detects that the substance storage is coupled to the inhalation device, cause at least one processor to switch from a standby mode to an operation mode, wherein the operation mode comprises vaporing a substance received from the substance storage when coupled to the inhalation device;
  requesting and receiving authentication information from the substance storage after the switching from the standby mode to the operation mode, and
  authenticating the substance storage.

10. The method of claim 9, further comprising:
  coupling or decoupling the passive detection circuit to or from a power supply using a switch.

11. The method of claim 9, further comprising:
  providing a wake-up signal to the at least one processor of the inhalation device.

12. The method of claim 11,
  wherein the wake-up signal is an interrupt pulse.

13. The method of claim 9, further comprising:
  providing a voltage having a first value in the case that the substance storage is decoupled from the inhalation device, and a second value different from the first value in the case that the substance storage is coupled to the inhalation device.

14. A method of operating an inhalation system having a substance storage and an inhalation device, the method comprising:
  alternatingly coupling the substance storage to the inhalation device and removing the substance storage from the inhalation device;
  passively detecting, by a passive detection circuit, whether the substance storage is coupled to the inhalation device, by pulling up or pulling down a voltage signal to detect whether the substance storage is coupled to the inhalation device;
  in case the passive detection circuit detects that the substance storage is coupled to the inhalation device, causing at least one processor to switch from a standby mode to an operation mode, wherein the operation mode comprises vaporing a substance received from the substance storage when coupled to the inhalation device;
  requesting and receiving authentication information from the substance storage after the switching from the standby mode to the operation mode; and
  authenticating the substance storage.

15. The inhalation device of claim 1, wherein the passive detection circuit is coupled between the electronic interface and the at least one processor directly.

* * * * *